United States Patent [19]

Sancoff et al.

[11] Patent Number: 5,080,652
[45] Date of Patent: Jan. 14, 1992

[54] INFUSION APPARATUS

[75] Inventors: Gregory E. Sancoff, Leucadia; Frederic P. Field, Cardiff, both of Calif.

[73] Assignee: Block Medical, Inc., Carlsbad, Calif.

[21] Appl. No.: 492,982

[22] Filed: Mar. 12, 1990

Related U.S. Application Data

[63] Continuation-in-part of Ser. No. 429,313, Oct. 31, 1989.

[51] Int. Cl.$^5$ ............................................. A61M 37/00
[52] U.S. Cl. ............................. 604/132; 222/95; 222/105; 222/103
[58] Field of Search ....................... 604/131, 132, 133; 128/DIG. 12; 222/95, 96, 214, 215, 105, 103

[56] References Cited

U.S. PATENT DOCUMENTS

| | | | |
|---|---|---|---|
| 515,288 | 2/1894 | Harsin | 604/132 |
| 3,412,906 | 11/1968 | Dinger | 222/183 |
| 3,468,308 | 9/1969 | Bierman | 604/141 |
| 3,469,578 | 9/1969 | Bierman | 604/132 |
| 3,486,539 | 12/1969 | Jacuzzi | 141/329 |
| 3,506,005 | 4/1970 | Gilin et al. | 604/132 |
| 3,883,046 | 5/1975 | Thompson et al. | 222/95 |
| 3,895,631 | 7/1975 | Buckles et al. | 604/132 |
| 3,961,725 | 6/1976 | Clark | 222/1 |
| 3,993,069 | 11/1976 | Buckles et al. | 604/132 |
| 4,140,117 | 2/1979 | Buckles et al. | 604/132 |
| 4,201,207 | 5/1980 | Buckles et al. | 604/132 |
| 4,318,400 | 3/1982 | Peery et al. | 604/18 |
| 4,386,929 | 6/1983 | Peery et al. | 604/132 |
| 4,419,096 | 12/1983 | Leeyer | 604/132 |
| 4,452,473 | 6/1984 | Ruschke | 285/81 |
| 4,597,758 | 7/1986 | Aalto et al. | 604/256 |
| 4,702,397 | 10/1987 | Gortz | 222/211 |
| 4,722,732 | 2/1988 | Martin | 604/132 |
| 4,769,008 | 9/1988 | Hessel | 604/132 |
| 4,915,693 | 4/1990 | Hessel | 604/132 |

*Primary Examiner*—Gene Mancene
*Assistant Examiner*—Michael Lynch
*Attorney, Agent, or Firm*—Baker, Maxham, Jester & Meador

[57] ABSTRACT

A liquid infuser apparatus includes an elastic sleeve mounted on an elongated member and within a spherical housing to enable it to expand naturally to maintain a constant pressure over the infusion period. An alternate embodiment includes a holding reservoir that may be pre-filled, and a pressure reservoir that is loaded from the holding reservoir preparatory to infusion.

20 Claims, 2 Drawing Sheets

INFUSION APPARATUS

REFERENCE TO RELATED APPLICATIONS

The present application is a continuation-in-part of our co-pending application Ser. No. 07/429,313, filed Oct. 31, 1989, and entitled INFUSION APPARATUS.

BACKGROUND OF THE INVENTION

The present invention relates to liquid dispensing apparatus and pertains particularly to an improved infuser apparatus for delivering intravenous drugs at a controlled rate to a patient.

It is often necessary to intravenously supply patients with pharmaceutically active liquids over a long period of time at a controlled rate. It is desirable that this be accomplished while the patient is in an ambulatory state. A few devices have been developed in the past for accomplishing this purpose.

The prior art devices typically comprise an elastic bladder forming a liquid container mounted in an elongated cylindrical housing, and having a flow control valve or device and tubing for supply of the liquid to the patient. The elastic walls of the bladder expand along the walls of the cylindrical housing when filled with the liquid, and provide the pressure for expelling the liquid. These prior art devices are typically filled by hand by means of a syringe which often require an inordinate amount of force.

Another drawback to the prior art devices is that the bladder is forced to expand into an unnatural elongated configuration along the housing walls as the container is filled. As a result of this unnatural configuration, the pressure of the bladder and the flow rate of the unit varies widely with the volume of liquid therein. Therefore, they do not have a reasonably stable pressure and flow rate over the infusion period.

Most of such devices either have a flow rate that decreases with pressure, which decreases with volume, or one that remains roughly constant until the end where it surges. Attempts have been made to control pressure and flow rates by means of complicated and expensive flow control valves and devices. Other approaches have utilized exotic and expensive elastic materials in an effort to control the pressures and flow rates.

In our aforementioned application, we disclose an apparatus for solving the aforementioned problems of the prior art. However, one problem remains, namely that the materials that provide optimum elasticity do not have sufficient chemical inertness for medical application. Similarly, materials that are sufficiently chemically inert for medical or pharmaceutical use are not sufficiently elastic to serve the function of an effective inflatable bladder.

It is desirable that the bladder of an inflatable bladder infuser be chemically inert in order to avoid contamination of the medication, and that the pressure and flow rate be reasonably constant over the infusion period.

Accordingly, it is desirable that an improved infuser apparatus be available.

SUMMARY AND OBJECTS OF THE INVENTION

It is the primary object of the present invention to provide an improved liquid infuser apparatus.

In accordance with a primary aspect of the present invention, a liquid infuser apparatus comprises an elastic reservoir mounted within a spherical chamber, and comprising an inner inert layer and an outer elastic capable of maintaining a substantially constant pressure over the range of the infusion cycle.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
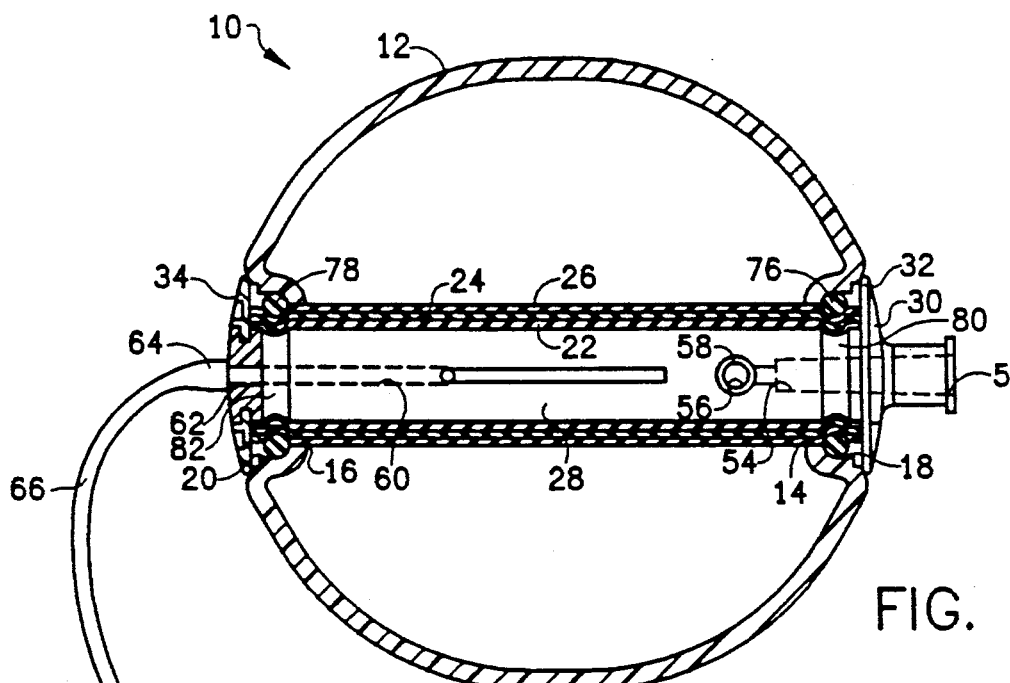
FIG. 1 is a side elevation in section view of a preferred embodiment of the invention.
Figure 1:
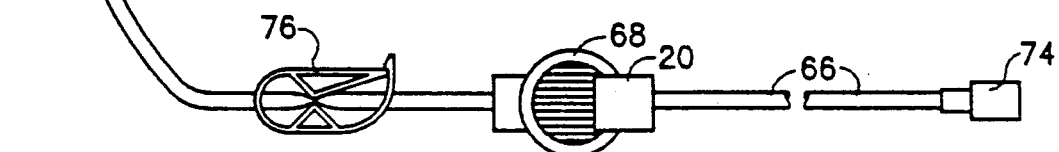
Figure 2:
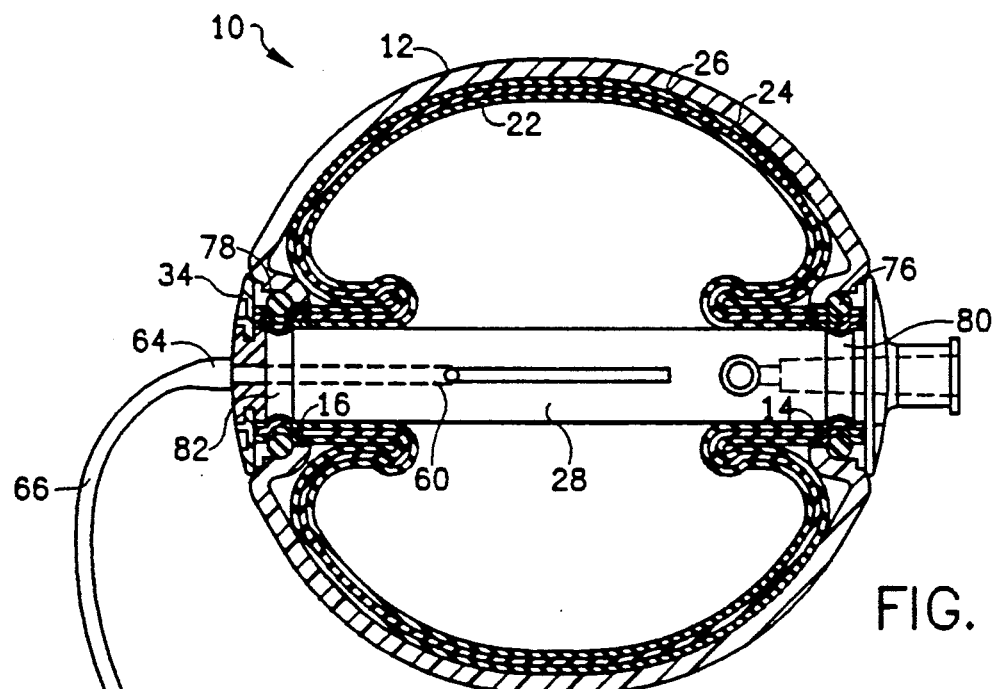
FIG. 2 is a view like FIG. 1 of the embodiment of FIG. 1 with the bladder shown inflated.
Figure 2:
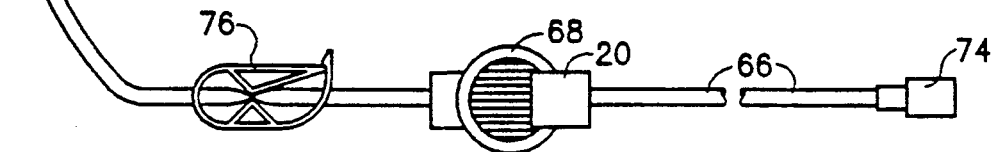
Figure 3:
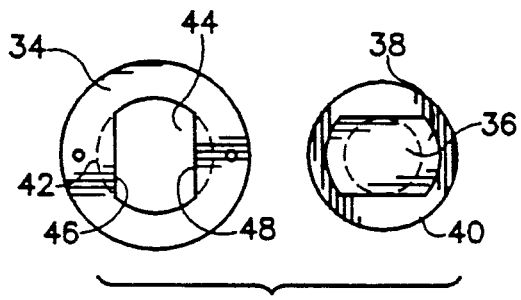
FIG. 3 is an end view of the central support member retaining means.

Referring to the drawings, and particularly to FIGS. 1-2, there is illustrated a preferred embodiment of the invention, wherein the infuser pump is separate from the charging or filler pump. Moreover, it may be filled by any suitable means, such as a syringe or any other pressurizing means. As illustrated in FIGS. 1 and 2, an infuser pump, substantially like the FIGS. 9-11 embodiments of our prior application, is designated generally by the numeral 10 and comprises an outer substantially spherical housing of a size to accommodate the necessary volume of intravenous fluid to be pumped.

The housing 12 has a substantially spherical configuration and is provided with coaxial, or more particularly aligned bores or ports 14 and 16, in which is mounted an inflatable bladder assembly. The housing 12 may be made of unitary construction, such as by blow molding, or may be of two identical half shells assembled. The ports are formed in axial recesses 18 and 20. The inflatable bladder assembly comprises a first or inner elongated semi-elastic sleeve 22, and a pair of outer elongated latex rubber elastic sleeves 24 and 26 mounted on an elongated central cylindrical support member 28. The inner sleeve 22 is preferably made of a drug compatibility rubber with low leach characteristics that meets USP class 6 testing standards.

A preferred rubber material for the inner sleeve 22 is a class of thermoplastic rubber sold under the mark KRATON by Shell Chemical Company of Houston, Texas. These materials are available as KRATON D and G 2000 series rubber, and have FDA status for use in certain applications or ingredients of articles for food contact. These materials have less than optimum elastic characteristics, and are referred to herein as semi-elastic. When stretched, they return to a position of about 75 to about 90 percent of original configuration.

The outer sleeves 24 and 26 are preferably made of a natural latex rubber with excellent elastic characteristics. A material with good elastic characteristics returns from a stretched condition to its original un-stressed or stretched condition. A good elastic material also has a uniform elastic force over the range stretched. Natural latex rubbers are the preferred material for the outer sleeves membranes 24 and 26.

The central support member 28 is preferably of a generally elongated cylindrical configuration, with an annular radially extending retaining flange 30 on one end for engaging a shoulder 32 on the housing 12. The opposite end of the support member 28 includes a bayonet type coupling with a retaining nut 34. The central support member may be constructed of any suitable pharmaceutically compatible material, such as metals, plastics, glass, etc.

The coupling comprises a generally rectangular projection 36, with shoulders 38 and 40 formed by annular slots in which the retainer nut rotates. The retainer nut 34 included a recess 42, with a rectangular opening 44 for receiving projection 36 on the end of support member 28. A pair of side lips 46 and 48 extend under shoulders 38 and 40 when the nut is rotated 90 degrees for retaining the nut in place and the support member 28 in the housing bores. The nut 34 rests in annular recess 50 surrounding recess 20.

Figure 4:
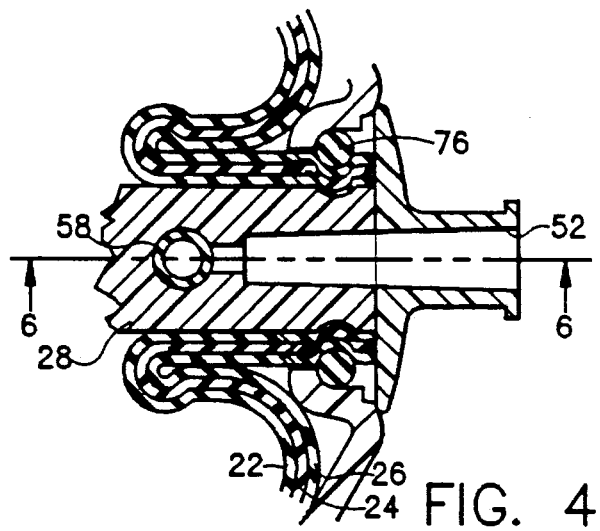
FIG. 4 is an enlarged detailed view of the check valve assembly of the embodiment of FIG. 1.
Figure 5:
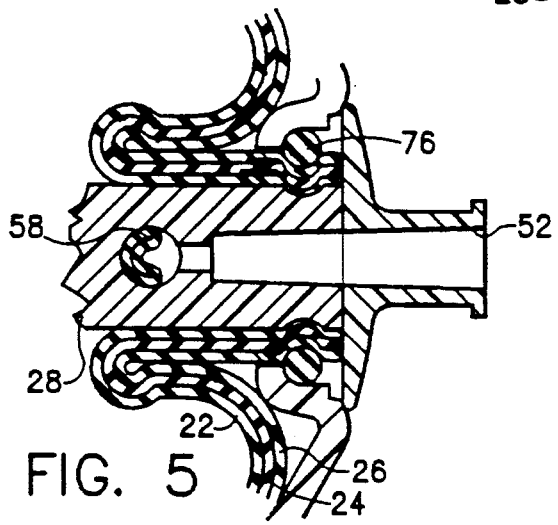
FIG. 5 is a view like FIG. 4 showing the valve open.
Figure 6:
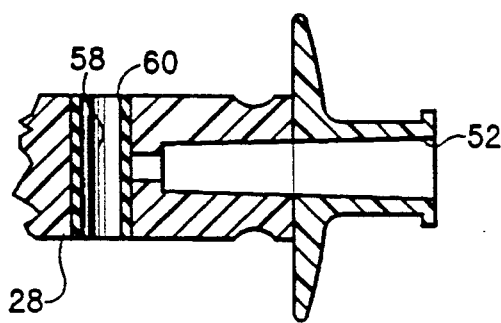
FIG. 6 is a section view taken generally on lines 6—6 of FIG. 4.

The support member 28 includes an inlet port 52 communicating by means of a passage 54, including a one-way valve 56, 59 with the interior of the membrane or sleeve 22. Any suitable check valve may be used to permit uncoupling of the filling unit without leakage of fluid from the pressurized bladder. However, a valve as illustrated in FIGS. 4-6 is preferred. The check valve comprises a cross throughbore 56 communicating with the end of passage 54, and in which is slip fitted an elastic tube 58, which may be of a suitable rubber such as silicone. The tube 58 covers the end of passage 54 to prevent back flow from inside the bladder formed by sleeve 22. The tube 58 collapses, as shown in FIG. 5, in response to higher pressure in passage 54 enabling flow of liquid into sleeve 22.

An outlet passage 60 in support member 28 communicates via an outlet port 62 and suitable coupling assembly 64, with an outlet or intravenous feeding line comprising a two-part tube 66, which includes a filter 68, and may include flow control means 70 and a male luer lock adaptor. The outlet line may be controlled by a suitable valve assembly (not shown) or preferably by the well known type clamp known as a Roberts clamp 76. The luer lock has a valve that closes the outlet port when the feeding line is uncoupled therefrom. The coupling is effective to open the outlet valve when coupled to the outlet fitting. Such luer locks are well known off-the-shelf items for I.V. delivery systems. The delivery tubes 66 may be selected in size and length to and aid in maintaining a predetermined pressure and flow rate. A suitable tube size for the particular application is 0.088 inch O.D. by 16.5 inch in length. Orifices or other means, such as flow regulating capillary tubes may be also used in controlling the flow.

The elastic sleeves 24 and 26 are mounted over the sleeve 22. Sleeves 24 and/or 26 may be stretched radially when in position over sleeve 22, e.g. 24 is stretched radially over 22, with 26 slip fit over the assemblies of 22 and 24. The outer bladder 26 slips radially over the assembly of 22 and 24. The composite assembly of 22, 24, 26 is slideably engaged with a slip fit over the mandrel or support member 28. Radial stretching of the bladder 24 compensates for material 22's less than perfect elasticity. More specifically, the wall thickness and amount of stretch of bladder 24 are selected to just compensate for bladder 22's material less than perfect elasticity. The initial strain conditions and bladder wall thicknesses are also chosen to minimize the non-linearity exhibited in a bladder's stress versus strain.

It is well known that a single bladder infusion device constrained at both ends exhibits a highly non-linear stress versus strain relationship. This causes a time varying flow characteristic. The prior art required stretching the membrane both axially and radially over a mandrel to reduce this non-linear behavior and thus generate a more constant flow versus time. We have improved the state of the art by incorporating a chemically inert inner bladder and an elastic outer bladder. Further, we have devised a structure and method for maintaining constant flow versus time while the device is infusing by radially stretching an intermediate bladder over the inner bladder.

The inner semi-elastic drug compatible tube or membrane 22 is mounted on the cylindrical support member 28, preferably in a slightly snug but un-stretched radial fit, and essentially relaxed elongated or non-stretched longitudinal fit. The inner sleeve 22 preferably has what shall be called a slip fit on the support member. This slip fit is preferably with a clearance of on the order of about one-thousandths of an inch of the sleeve on the support. This provides a non-stretched fit, with essentially zero volume of the pressure chamber when in the non-stretched or totally relaxed state or mode.

The elastic sleeves 24 and 26 are respectively stretch fit and snug fit radially over the inner semi-elastic sleeve 22. The intermediate sleeve 24 is radially stretched up to about five percent over the inner sleeve 22 for compressing it. The outer sleeve 26 is slip fitted over the intermediate sleeve 24. All of these sleeves 22, 24, and 26 are fitted over the support member 28 and clamped at the ends by means of a pair of O-rings 76 and 78. These O-rings 76 and 78 bias the ends of the multiple sleeves into annular grooves 80 and 82 in the outer surface of the member 28. The O-rings 76 and 78 are held in place by the walls of the housing forming the recesses 18 and 20. The multiple sleeves when being filled tend to elongate and roll over the ends thereof as shown in FIG. 2. The support member 28 is of a fixed length and holds the ends of the sleeves at a fixed position. The multiple thin sleeves easily roll over the ends thereof as the bladder made up of the multiple sleeves fills and expands.

The pressure applied by the pressure chamber, formed by the multiple sleeves, will be substantially a function of the thickness of the wall of the elastic sleeve or sleeves. For example, a typical two to three (2-3) psi may be obtained by a wall thickness of about eighteen to twenty-thousandths (0.018-0.020) of an inch. In order to obtain higher pressure with superior uniformity, a multi-layered sleeve configuration as described hereinabove has been found to be preferred.

As illustrated in FIG. 1, a plurality of sleeves (three illustrated) 22, 23 and 24 are slip fitted (non-stretched) on the support member. The inner sleeve 22 is slip fitted on the support member 28, and a second sleeve 24 is slightly stretch fitted over the first sleeve 22. Thereafter, a third sleeve 26 is slip fitted over the intermediate sleeve 24. These are shown in the fully deflated position in FIG. 1 and in the fully inflated condition in FIG. 2, showing the fold or roll over the ends. These multiple layers have been found to be superior to the use of thicker membranes or sleeves to obtain higher and uniform pressures. The use of multiple layers also enables the use of a semi-elastic substantially chemically (medically) inert inner membrane or sleeve for contact with the infusible liquid. The multiple sleeves will roll or fold over at the ends, as illustrated in FIG. 2. Thus, to increase the pressure, additional sleeves of substantially the same thickness are used.

When being filled, the elastic multi sleeve membrane has a tendency to elongate, but expands into a spherical configuration (FIGS. 10 and 11 of our prior application). The sleeve is shown in the partially filled position in FIG. 10 and in the fully filled position in phantom.

The elongation is accommodated in this pump configuration by an accordion effect at the ends of the bladder, as shown in FIG. 2, wherein the bladder rolls over the ends thereof and outward along the support member 28 as it expands outward to fill the housing 12. The accommodation of the elastic membrane in the spherical configuration enables it to expand and contract in its natural fashion, and to maintain a substantially constant pressure and thereby flow rate over the intravenous injection period.

The layered or multiple sleeve configuration has been found to better accommodate the accordion fold and maintain a more uniform pressure than a thicker sleeve. The tubular elastic sleeve membranes are selected and mounted on the support member in a manner that enables them to roll or fold over at the ends when being filled.

In operation, an assembled infuser pump unit is selected, and the inlet port 52 is secured to a source of fluid under pressure. As fluid is being introduced into the inlet, the valve 58 collapses in FIG. 5 as fluid flows into the inner sleeve or membrane 22. As the reservoir or bladder formed by the sleeves begins to fill, it expands and attempts to elongate. The ends of the sleeves begin to fold and roll over the ends thereof as in FIG. 2. The bladder forms a substantially spherical shape as its natural form of expansion. The roll at the ends accommodates this expansion and aids in maintaining a substantially constant pressure over the range of infusion.

As the bladder deflates, the outer elastic membranes force the inner semi-elastic membrane back to substantially its original position. This helps to evacuate the entire volume of fluid. It also will be appreciated that any form of pressurized filling apparatus may be used. For example, the squeeze fill embodiment of FIG. 1 of our prior application could be utilized with this infusion pump.

While we have illustrated and described our invention by means of specific embodiments, it is to be understood that numerous changes and modifications may be made therein without departing from the spirit and scope of the invention as defined in the appended claims.

We claim:

1. An apparatus for dispensing a liquid under pressure at a substantially constant flow rate over a period of time comprising:
   a housing having a chamber for accommodating natural expansion of an elastic bladder to a predetermined volume and an opening into said chamber;
   an elongated substantially cylindrical non-extensible support member disposed in said chamber and having an end disposed at said opening;
   a pressure reservoir comprising an inner chemically inert bladder and an outer elastic bladder mounted on said support member, said inert bladder being in non-stretched surface contact with said support member, and said inert bladder and said elastic bladder sealingly secured at longitudinally spaced fixed positions thereon in said chamber for holding a liquid in a pressurized state for dispensing therefrom;
   inlet means for introducing a liquid into said pressure reservoir; and
   outlet means for dispensing liquid from said pressure reservoir to a selected site.

2. An apparatus for dispensing a liquid under pressure according to claim 1 wherein:
   said chemically inert bladder is formed of a semi-elastic material and is expandable to a predetermined volume.

3. An apparatus for dispensing a liquid under pressure according to claim 1 wherein:
   said inner bladder comprises a semi-elastic sleeve slip fitted over said support member and secured thereto with the ends thereof extending axially outward in a manner to enable folding over at the ends when being filled; and
   said outer elastic bladder comprises an elastic sleeve mounted over said inner sleeve and secured to said support member with the ends thereof extending axially outward in a manner to enable folding over at the ends when being filled.

4. An apparatus for dispensing a liquid under pressure according to claim 3 wherein:
   said support member is an elongated generally cylindrical mandrel mounted in said housing and having opposite ends exposed to the exterior of said housing, said inlet means comprises an inlet port in one end of said mandrel, and said outlet means comprises an outlet port in the other end of said mandrel; and
   said inner and outer sleeves are sealingly clamped at opposite ends thereof around opposite ends of said mandrel.

5. An apparatus for dispensing a liquid under pressure according to claim 1 wherein:
   said support member is an elongated generally cylindrical mandrel mounted in said housing and having opposite ends exposed to the exterior of said housing, an inlet port in one end of said mandrel, and an outlet port in the other end of said mandrel; and
   said elastic sleeve is sealingly clamped at opposite ends thereof around opposite ends of said mandrel on the exterior of said housing;

6. An apparatus for dispensing a liquid under pressure according to claim 1 wherein said inner bladder is a sleeve made of Kraton rubber.

7. An apparatus for dispensing a liquid under pressure according to claim 6 wherein:
   said support member is an elongated generally cylindrical mandrel mounted in said housing and having opposite ends exposed to the exterior of said housing, an inlet port in one end of said mandrel, and an outlet port in the other end of said mandrel; and
   said elastic bladder comprises a first elastic sleeve radially stretched over said inner sleeve for precompressing said inner sleeve, and a second elastic sleeve slip fitted over said first elastic sleeve, and said sleeves are sealingly clamped at opposite ends thereof around opposite ends of said mandrel.

8. An apparatus for dispensing a liquid under pressure according to claim 1 wherein:
   said support member is an elongated generally cylindrical mandrel mounted in said housing and having opposite ends exposed to the exterior of said housing, an inlet port in one end of said mandrel, and an outlet port in the other end of said mandrel; and said elastic bladder comprises a first elastic sleeve radially stretched over said inert bladder for compressing said inner bladder, and a second elastic sleeve slip fitted over said first elastic sleeve, and said sleeves are sealingly clamped at opposite ends thereof around opposite ends of said mandrel.

9. An apparatus for dispensing a liquid under pressure according to claim 1 wherein:

said elastic bladder comprises a first elastic sleeve slip fit mounted on said support member in a non-stretched condition; and a second elastic sleeve mounted over said first elastic sleeve, said sleeves being secured to said support member with the ends thereof extending axially outward so that said sleeves fold over onto the ends thereof when being filled to said predetermined volume.

10. An apparatus for dispensing a liquid under pressure according to claim 9 wherein said inner bladder is a sleeve made of Kraton rubber.

11. An apparatus for dispensing a liquid under pressure according to claim 1 wherein:

said support member is an elongated substantially cylindrical member extending substantially through said housing; and said elastic bladder comprises a plurality of elastic sleeves extending over and along said support member and sealingly clamped thereto at opposite ends thereof, with said opposite ends extending axially outward so that said sleeves fold over onto the ends thereof when inflated.

12. An apparatus for dispensing a liquid under pressure at a predetermined substantially constant flow rate over a period of time comprising:

a housing having a substantially spherical chamber;

an elongated generally cylindrical non-extensible support member disposed in and extending through said chamber;

a substantially chemically inert first sleeve slip fit mounted on said support member in non-stretched surface contact therewith, and an elastic second sleeve mounted snugly over said first sleeve in said chamber, the ends of said first sleeve and said second sleeve sealingly secured at spaced fixed positions on said support member for defining a pressure reservoir for holding a liquid in a pressurized state for dispensing therefrom;

inlet means in said support member for introducing a liquid into said elastic sleeve; and outlet means in said support member for conveying a liquid from said pressure chamber to a selected site.

13. An apparatus for dispensing a liquid under pressure according to claim 12 wherein:

said support member is an elongated generally cylindrical mandrel mounted in said housing and having opposite ends exposed to the exterior of said housing, said inlet means comprises an inlet port in one end of said mandrel, and said outlet means comprises an outlet port in the other end of said mandrel; and said first sleeve and said second sleeve are sealingly clamped at opposite ends thereof around opposite ends of said mandrel.

14. An apparatus for dispensing a liquid under pressure according to claim 13 wherein said first sleeve is made of Kraton rubber.

15. An apparatus for dispensing a liquid under pressure according to claim 14 further comprising a third elastic sleeve mounted over said elastic second sleeve.

16. An apparatus for dispensing a liquid under pressure according to claim 15 wherein said second sleeve is pre-stretched radially over said first sleeve.

17. An apparatus for dispensing a liquid under pressure at a substantially constant flow rate over a period of time comprising:

a housing having a substantially spherical chamber for containing a pressure reservoir of a predetermined volume;

an elongated non-extensible generally cylindrical support member disposed in and extending through said chamber;

an expansible elastic pressure reservoir mounted on said support member in said chamber for holding said liquid under pressure during dispensing thereof;

said elastic pressure reservoir comprises a substantially chemically inert first sleeve slip fit mounted on said support member in non-stretched surface contact therewith, and an elastic second sleeve snugly mounted with a slightly radial pre-stretch over said first sleeve in said chamber for defining a pressure reservoir for holding in liquid in a pressurized state for dispensing therefrom, said first sleeve and said second sleeve each sealingly secured at the ends thereof to said support member at spaced fixed positions thereon and expandable naturally to a substantially spherical configuration at said predetermined volume;

inlet means in said support member for introducing a liquid into said elastic sleeve; and discharge means for conveying a liquid from said pressure reservoir to a selected site.

18. An apparatus for dispensing a liquid under pressure according to claim 17 wherein:

said housing is formed of a hard transparent plastic and of a spherical configuration.

19. An apparatus for dispensing a liquid under pressure according to claim 18 wherein said first sleeve is made of Kraton rubber.

20. An apparatus for dispensing a liquid under pressure according to claim 19 wherein said pressure reservoir includes a third sleeve snug fit over said second sleeve.

* * * * *